(12) United States Patent
Kurosawa et al.

(10) Patent No.: US 8,278,097 B2
(45) Date of Patent: Oct. 2, 2012

(54) METHOD FOR FORMING EMBRYOID BODIES

(75) Inventors: Hiroshi Kurosawa, Koufu (JP); Shujiro Sakaki, Tsukuba (JP)

(73) Assignee: NOF Corporation, Tokyo (JP)

( * ) Notice: Subject to any disclaimer, the term of this patent is extended or adjusted under 35 U.S.C. 154(b) by 602 days.

(21) Appl. No.: 12/480,156

(22) Filed: Jun. 8, 2009

(65) Prior Publication Data

US 2009/0246871 A1   Oct. 1, 2009

Related U.S. Application Data

(62) Division of application No. 10/562,015, filed as application No. PCT/JP2004/008970 on Jun. 25, 2004, now Pat. No. 7,648,833.

(30) Foreign Application Priority Data

Jun. 25, 2003   (JP) .................................. 2003-181342

(51) Int. Cl.
*C12N 5/00*   (2006.01)

(52) U.S. Cl. ........ 435/325; 435/352; 435/354; 435/355; 435/363; 435/366; 435/283.1; 435/375

(58) Field of Classification Search ................... 435/325, 435/283.1, 263, 366, 352, 354, 355, 375
See application file for complete search history.

(56) References Cited

U.S. PATENT DOCUMENTS

| 5,648,442 | A  | 7/1997 | Bowers et al. |
| 6,284,854 | B1 | 9/2001 | Bowers et al. |
| 6,420,453 | B1 | 7/2002 | Bowers et al. |

FOREIGN PATENT DOCUMENTS

| EP | 1152242    | 11/2001 |
| JP | 54-36025   | 3/1979  |
| JP | 03-039309  | 2/1991  |
| JP | 5-336956   | 12/1993 |
| JP | 09-183819  | 7/1997  |
| WO | 00/70021   | 11/2000 |

OTHER PUBLICATIONS

English machine translation of JP2002-543828 downloaded from the JPO on Dec. 19, 2011, 7 pages.*
Kazuhiko Ishihara, etal.; Inhibition of fibroblast cell adhesion on substrate by coating with 2-methacryloyloxethyl phosphorylcholine polymers; J. Biomater: Sci. Polymer Edn. vol. 10, No. 10, pp. 1047-1061 (1999).
Yasuhiko Iwasaki, et al.; The effect of the chemical structure of the phospholipid polymer on fibronectin adsorption and fibroblast adhesion on the gradient phospholipid surface; Biomaterials 20 (1999) 2185-2191.

* cited by examiner

*Primary Examiner* — Susan Hanley
(74) *Attorney, Agent, or Firm* — Sughrue Mion, PLLC

(57) ABSTRACT

The invention relates to a vessel for embryoid formation used for forming embryoid bodies from ES cells easily without complicated technique, and to a method for forming embryoid bodies easily and efficiently using the vessel. The method includes the steps of (A) providing a vessel for embryoid formation having a coating layer formed from a compound having a particular PC-like group on a vessel surface defining a region for floating culture of ES cells, and (B) floating culturing ES cells in the vessel to form embryoid bodies.

6 Claims, 3 Drawing Sheets

METHOD FOR FORMING EMBRYOID BODIES

This application is a Divisional of application Ser. No. 10/562,015 filed May 12, 2006 (issued as U.S. Pat. No. 7,648,833), which is a 371 application of PCT/JP2004/008970 filed Jun. 25, 2004, which claims priority from Japanese Patent Application No. 2003-181342 filed Jun. 25, 2003. The entire disclosures of these prior applications are hereby incorporated by reference.

FIELD OF ART

The present invention relates to a vessel for embryoid formation for use in forming embryoid bodies, and a method for forming embryoid bodies.

BACKGROUND ART

Embryonic stem cells (ES cells) are capable of differentiating into various types of cells even in vitro. In vitro differentiation of ES cells is performed by floating culture to form pseudo-embryos, called embryoid bodies, or by coculture with cells, such as stromal cells, that support differentiation and proliferation of ES cells. It is known that ES cells differentiate into various types of cells when the cells are cultured to high density without LIF (Leukemia Inhibitory Factor), and then floating cultured so as not to adhere to a culture vessel, such as a petri dish, to form cell aggregates. The cell aggregates formed by floating culture are called embryoid bodies (EB), and the floating culture is the most common method for differentiating ES cells in vitro.

An embryoid body has a ball-like structure composed of a bilayer of cells. The outer layer corresponds to visceral endoderm, the inner layer corresponds to embryonic ectoderm, and the two endoderms are separated by a basement membrane. This structure is quite similar to that of a cylindrical embryo, which is a day 6 mouse embryo. As far as this similarity is concerned, this structure resembles the normal stage of embryogenesis. In embryoid bodies, mesoderm is also induced, and cardiomyocytes, blood cells, and even primitive vascular networks are developed. When plated on a culture petri dish and cultured further, the embryoid bodies differentiate into various types of cells, including neurons, keratinocytes, chondrocytes, adipocytes, and the like. It has recently been confirmed that the cells that differentiate via formation of embryoid bodies are differentiated not only into somatic cells, but also into a germ cell lineage. As such, formation of embryoid bodies is useful for demonstrating pluripotency of ES cells.

For embryoid formation, so-called a "hanging drop method" is widely used, which is devised to prevent adhesion of ES cells to a culture vessel. There are known hanging drop method 1, wherein ES cells are added to and cultured in the drops having from the lid of a glass container, and hanging drop method 2, wherein ES cells are placed over mineral oil previously placed in a culture vessel, and cultured. In hanging drop method 1, however, the hanging drops must be prevented from falling which causes extreme complexity in culture preparation and handling. In hanging drop method 2 using mineral oil, on the other hand, the interface between the mineral oil and the overlaid cell suspension must be prevented from being disrupted, and also no microscopic examination is allowed before the generated embryoid bodies are transferred to another culture vessel, which impedes researches in embryogenesis.

Phosphorylcholine group-containing polymers have been revealed to have properties ascribable to their phospholipid-like structure originated from biomembranes, such as blood compatibility, complement activation, and nonadsorbability of biomaterials, and development of bio-related materials making good use of such functions has been actively made. For example, Patent Publication 1 discloses a method of producing 2-methacryloyloxyethyl phosphorylcholine (abbreviated as MP/C hereinbelow) and excellent biocompatibility of polymers thereof. Patent Publication 2 discloses usefulness of copolymers of MP/C and methacrylate as medical materials due to their ability to hardly allow platelet adhesion or aggregation and plasma protein adhesion. Patent Publication 3 discloses medical materials prepared from a copolymer having a phosphorylcholine-like group in its side chain. Patent Publications 4 and 5 disclose excellent biocompatibility achieved by coating a resin surface with a polymer having a phosphorylcholine-like group. Patent Publication 6 discloses a separating agent and a method of separation and collection for separating and collecting blood cells, cell lines, or primary culture cells, using polyethylene terephthalate coated with a polymer having a phosphorylcholine-like group.

It is not known, however, to use a vessel coated with a polymer having a phosphorylcholine-like group, for floating culture of ES cells.

Patent Publication 1: JP-54-36025-A
Patent Publication 2: JP-3-39309-A
Patent Publication 3: JP-9-183819-A
Patent Publication 4: JP-6-502200-A
Patent Publication 5: JP-7-502053-A
Patent Publication 6: JP-2002-098676-A

SUMMARY OF THE INVENTION

It is an object of the present invention to provide a vessel for embryoid formation that is used for easy formation of embryoid bodies from ES cells without complicated techniques.

It is another object of the present invention to provide a method for forming embryoid bodies that enables easy culture of ES cells to form embryoid bodies without complicated techniques.

According to the present invention, there is provided a vessel for embryoid formation for use in floating culture of embryonic stem cells (ES cells) to form embryoid bodies, comprising a coating layer formed from a compound having a phosphorylcholine-like group represented by the formula (1) (abbreviated as PC-like group hereinbelow), on a vessel surface defining a region for floating culture of ES cells:

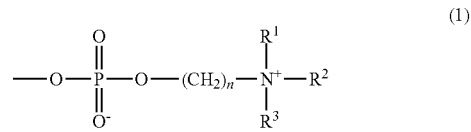

wherein $R^1$, $R^2$, and $R^3$ are the same or different groups, and each stands for a hydrogen atom, an alkyl or hydroxyalkyl group having 1 to 6 carbon atoms; and n is an integer of 1 to 4.

According to the present invention, there is provided a method for forming embryoid bodies, comprising the steps of:

(A) providing a vessel for embryoid formation having a coating layer formed from a compound having a PC-like group represented by the formula (1), on a vessel surface defining a region for floating culture of ES cells, and (B) floating culturing ES cells in said vessel for embryoid formation to form embryoid bodies.

In the method for forming embryoid bodies of the present invention, since the vessel for embryoid formation of the present invention is used in culture, embryoid bodies may be formed from ES cells easily and efficiently without complicated techniques which are required for culturing ES cells by the conventional hanging drop method. Since the vessel for embryoid formation of the present invention has a coating layer formed from a compound having a PC-like group on a desired surface, the present vessel is useful for forming embryoid bodies from ES cells.

PREFERRED EMBODIMENTS OF THE INVENTION

Figure 1:
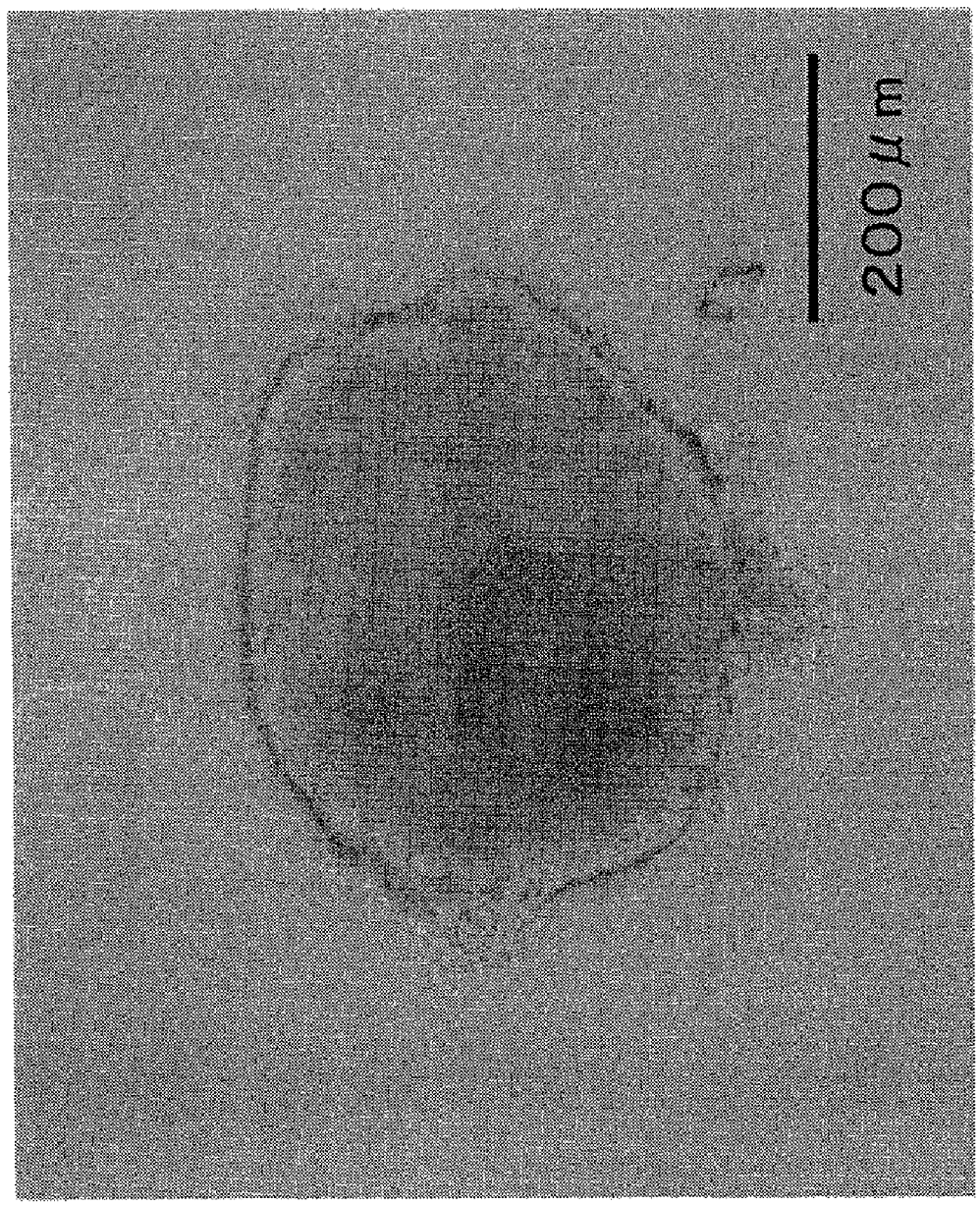
FIG. 1 is a photocopy of a phase contrast micrograph of an embryoid body prepared in Example 2-1.

The present invention will now be explained in detail.

The vessel for embryoid formation according to the present invention is for use in floating culture of ES cells to form embryoid bodies. The present vessel is characterized by its coating layer formed from a compound having a PC-like group represented by the formula (1), on a vessel surface defining a region for floating culture of ES cells.

In the formula (1), $R^1$, $R^2$, and $R^3$ are the same or different groups, and each stands for a hydrogen atom, an alkyl or hydroxyalkyl group having 1 to 6 carbon atoms.

The alkyl group having 1 to 6 carbon atoms may be, for example, a methyl, ethyl, propyl, butyl, pentyl, hexyl, cyclohexyl, or phenyl group. The hydroxyalkyl group having 1 to 6 carbon atoms may be, for example, a hydroxymethyl, 2-hydroxyethyl, 3-hydroxypropyl, 4-hydroxybutyl, 5-hydroxypentyl, or 6-hydroxyhexyl group.

The coating layer may be formed on a vessel surface using a compound having the PC-like group represented by the formula (1) by a method of, for example, fixing a reaction reagent containing the compound having a PC-like group on a desired surface of a vessel by chemical modification, fixing a polymer having a PC-like group on a desired surface of a vessel by coating, or fixing a polymer having a PC-like group on a desired surface of a vessel by chemical bonding. Among these, the coating method is particularly preferred for easy and convenient formation of a uniform coating layer of the compound having a PC-like group.

The polymer having a PC-like group may be any polymer as long as it has a PC-like group represented by the formula (1), and may preferably be, for example, at least one of a homopolymer of monomer (M) represented by the formula (2) having a PC-like group, and a copolymer of monomer (M) and another monomer:

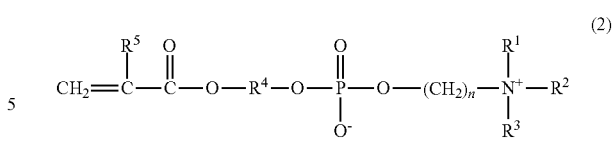

wherein $R^1$, $R^2$, $R^3$, and n are the same as those in the formula (1); $R^4$ stands for an alkyl group having 1 to 6 carbon atoms; and $R^5$ stands for a hydrogen atom or a methyl group.

Monomer (M) represented by the formula (2) may be, for example, 2-((meth)acryloyloxy)ethyl-2'-(trimethylammonio) ethylphosphate, 3-((meth)acryloyloxy)propyl-2'-(trimethylammonio)ethylphosphate, 4-((meth)acryloyloxy)butyl-2'-(trimethylammonio) ethylphosphate, 5-((meth)acryloyloxy)pentyl-2'-(trimethylammonio)ethylphosphate, 6-((meth)acryloyloxy) hexyl-2'-(trimethylammonio)ethylphosphate, 2-((meth)acryloyloxy)ethyl-2'-(triethylammonio) ethylphosphate, 2-((meth)acryloyloxy)ethyl-2'-(tripropylammonio) ethylphosphate, 2-((meth)acryloyloxy)ethyl-2'-(tributylammonio)ethylphosphate, 2-((meth)acryloyloxy)ethyl-2'-(tricyclohexylammonio) ethylphosphate, 2-((meth)acryloyloxy)ethyl-2'-(triphenylammonio) ethylphosphate, 2-((meth) acryloyloxy) propyl-2'-(trimethylammonio)ethylphosphate, 2-((meth)acryloyloxy)butyl-2'-(trimethylammonio) ethylphosphate, 2-((meth)acryloyloxy)pentyl-2'-(trimethylammonio)ethylphosphate, or 2-((meth)acryloyloxy) hexyl-2'-(trimethylammonio) ethylphosphate.

Among these, 2-((meth)acryloyloxy)ethyl-2'-(trimethylammonio)ethylphosphate is preferred, and in particular, 2-(methacryloyloxy)ethyl-2'-(trimethylammonio)ethylphosphate (also called 2-methacryloyloxyethyl phosphorylcholine, abbreviated as MPC hereinbelow) is more preferred for its availability and capability of preventing adhesion of ES cells to the culture vessel to facilitate expression of their ability to form embryoid bodies.

Examples of another monomer used in preparing the copolymer may include hydrophobic monomers; (meth)acrylates containing a hydroxyl group, such as 2-hydroxyethyl (meth)acrylate, 2-hydroxybutyl (meth)acrylate, and 4-hydroxybutyl(meth)acrylate; monomers containing an ionic group, such as acrylic acid, methacrylic acid, styrenesulfonic acid, (meth)acryloyloxyphosphonic acid, and 2-hydroxy-3-(meth)acryloyloxypropyl trimethyl ammonium chloride; monomers containing nitrogen, such as (meth)acrylamide, aminoethylmethacrylate, and dimethylaminoethyl(meth) acrylate; polyethylene glycol (meth)acrylate; glycidyl(meth) acrylate; or a mixture of two or more of these.

Examples of the hydrophobic monomers may include straight or branched alkyl(meth)acrylate, such as methyl (meth)acrylate, ethyl(meth)acrylate, butyl(meth)acrylate, 2-ethylhexyl(meth)acrylate, lauryl(meth)acrylate, or stearyl (meth)acrylate; cyclic alkyl(meth)acrylate, such as cyclohexyl(meth)acrylate; aromatic (meth)acrylate, such as benzyl (meth)acrylate, or phenoxyethyl(meth)acrylate; hydrophobic polyalkylene glycol(meth)acrylate, such as polypropylene glycol(meth)acrylate; styrene monomers, such as styrene, methylstyrene, or chloromethylstyrene; vinyl ether monomers, such as methyl vinyl ether or butyl vinyl ether; vinyl ester monomers, such as vinyl acetate or vinyl propionate; or a mixture of two or more of these.

In the copolymer, the content of the unit derived from the hydrophobic monomers is preferably not more than 90 mol %, more preferably 20 to 90 mol % of all the units of the copolymer. Copolymers having a unit derived from a hydrophobic monomer have improved elution resistance. However, if the content of the unit derived from a hydrophobic monomer exceeds 90 mol %, the amount of the PC-like group represented by the formula (1) coated on the vessel surface is too small, and sufficient effect of the coating may not be exhibited.

The copolymer is given improved elution resistance when the copolymer contains a unit derived from monomers other than the hydrophobic monomers. This allows use of surfactants or organic solvents in the medium or the like, which is advantageous.

For example, a copolymer prepared using glycidyl (meth) acrylate may be reacted with the amino, carboxyl, or the like groups on the vessel surface to chemically bond the copolymer to the desired surface.

In the copolymer, the content of the units derived from monomers other than the hydrophobic monomers is preferably not more than 70 mol %.

The molecular weight of the homopolymer of monomer (M) represented by the formula (2) having a PC-like group, or of the copolymer of monomer (M) and another monomer, is usually 5000 to 5000000 in weight average molecular weight. For effectively preventing adhesion of ES cells to the culture vessel to allow expression of their ability to form embryoid bodies, and improving the elution resistance of the polymer, the molecular weight of the polymer is preferably 100000 to 2000000.

The amount of coating in the coating layer of the present invention may be evaluated by surface analysis. More specifically, the amount of coating may be evaluated by the ratio of the peak area P of phosphorus to the peak area C of carbon, i.e., the P/C value, based on the spectrum measured by the X-ray photoelectron spectroscopy. For allowing expression of the ability to form embryoid bodies, the P/C value is preferably in the range of 0.002 to 0.3, more preferably 0.01 to 0.2.

The type of the vessel for embryoid formation of the present invention is not particularly limited, and may be a conventional cell culture vessel, such as a cell culture dish, a cell culture multidish, a cell culture plate, a cell culture bag, or a cell culture flask. For obtaining embryoid bodies of an appropriate size, a cell culture dish or a cell culture plate is particularly preferred. The material of the vessel for embryoid formation is not particularly limited, and may be, for example, polystyrene, polypropylene, polyethylene, acrylic resins, glass, or metal. The vessel surface to be coated with the coating layer has preferably been subjected to surface treatment, such as corona treatment.

The coating layer may be formed at desired portions of the vessel surface using at least one of the homopolymer of monomer (M) and the copolymer of monomer (M) and another monomer, by, for example, dissolving the polymer in one of water, ethanol, methanol, isopropanol, and the like, or in a mixed solvent of water and ethanol, ethanol and isopropanol, or the like, and then soaking the vessel in the polymer solution, or spraying the polymer solution over the vessel.

When the copolymer has a functional group capable of chemical bonding, such as an epoxy, isocyanate, succinimide, amino, carboxyl, or hydroxyl group, in order for such a functional group to be chemically reacted with the amino, carboxyl, or hydroxyl group on the vessel surface, the vessel for embryoid formation may be prepared by dissolving a solution containing the copolymer in a solvent that is not reactive with the functional group capable of chemical bonding, to chemically bond the copolymer to the vessel surface to form the coating layer, and then washing away the unreacted polymer.

The method for forming embryoid bodies according to the present invention includes the steps of: (A) providing a vessel for embryoid formation having a coating layer formed from a compound having a PC-like group represented by the formula (1), on a vessel surface defining a region for floating culture of ES cells, and (B) floating culturing ES cells in the vessel for embryoid formation to form embryoid bodies.

The vessel provided in step (A) may be a vessel for embryoid formation according to the present invention, and all the vessels exemplified above may be employed as the vessel provided in step (A).

The floating culture of ES cells in step (B) may be carried out by floating culturing undifferentiated ES cells that have been cultured on feeder cells, in the vessel for embryoid formation by a conventional method under conventional conditions. Here, the culture liquid in the vessel for embryoid formation may be kept under static conditions or gently shaken.

The medium constituting the culture liquid may be a medium containing various growth factors used for the conventional hanging drop method, such as Iscove's modified Dulbecco's medium (IMDM medium).

The concentration of ES cells in the culture liquid may vary depending on the size, shape, or the like, of the vessel for embryoid formation provided in step (A), but may usually be in the range of $1.0 \times 10^2$ to $1.0 \times 10^6$ cells/mL. Specifically, when a 96-well plate is used as the vessel for embryoid formation, a preferred concentration of ES cells is $1.0 \times 10^3$ to $1.0 \times 10^5$ cells/mL for formation of embryoid bodies with good reproducivity.

EXAMPLES

The present invention will now be explained in more detail with reference to Examples and Comparative Examples, which do not intend to limit the present invention. In the Examples and Comparative Examples, the P/C value on the vessel surface was determined in accordance with the following method.

<Measurement of P/C Value on the Surface of Vessel for Embryoid Formation>

Spectrum of each element was measured with an X-ray photoelectron spectroscope (trade name "ESCA-3300", manufactured by SHIMADZU CORPORATION) at an X-ray irradiation angle of 900, and from the obtained peak areas of phosphorus and carbon elements, the P/C value was calculated in accordance with the following formula: P/C=Ap (peak area of phosphorus element)/Ac (peak area of carbon element)

Synthesis Example 1

35.7 g of MPC and 4.3 g of n-butylmethacrylate (BMA) (MPC/BMA =80/20 (by molar ratio)) were dissolved in 160 g of ethanol, placed in a four-neck flask, and bubbled with nitrogen for 30 minutes. 0.82 g of azobisisobutyronitrile was added at 60° C., and reacted for polymerization for 8 hours. The obtained polymer liquid was added dropwise into 3 L of diethyl ether under stirring, and the resulting precipitate was recovered by filtration, and vacuum dried at room temperature for 48 hours, to obtain 29.6 g of powder. The weight average molecular weight of the obtained powder measured by GPC under the following conditions, was found to be 153000. Compositional analysis by $^1$H-NMR revealed that MPC/BMA =80/20 (by molar ratio). The powder is designated as copolymer (A).

<Conditions of GPC>
(1) Sample: A sample was dissolved in a chloroform/methanol (6/4 (by volume)) mixed solvent containing 0.5 wt % lithium bromide to prepare a 0.5 wt % polymer solution. The amount of the sample solution used was 20 L.
(2) Column: Two PLgel 5 μm MIXED-C columns arranged in series (manufactured by POLYMER LABORATORIES LTD.) were used at a column temperature of 40° C., and a molecular weight calculating program with integrator (GPC program for SC-8020) manufactured by TOSOH CORPORATION was used.
(3) Eluting solvent: A chloroform/methanol (6/4 (vol %)) mixed solvent containing 0.5 wt % lithium bromide was used, at a flow rate of 1.0 mL/min.
(4) Detection: Differential refractive index detector
(5) Reference material: Polymethylmethacrylate (PMMA) (manufactured by POLYMER LABORATORIES LTD.)

Synthesis Example 2

38.0 g of MPC and 2.0 g of glycidyl methacrylate (GMA) (MPC/GMA 90/10 (by molar ratio)) were dissolved in 358 g of isopropanol, placed in a four-neck flask, and bubbled with nitrogen for 30 minutes. 2.18 g of a toluene solution of 20 wt % t-butyl peroxypivalate was added at 60° C., and reacted for polymerization for 5 hours. The obtained polymer liquid was added dropwise into 3 L of diethyl ether under stirring, and the resulting precipitate was recovered by filtration, and vacuum dried at room temperature for 4.8 hours, to obtain 28.4 g of powder. Compositional analysis of the powder by $^1$H-NMR revealed that MPC/GMA=90/10 (by molar ratio). The weight average molecular weight measured by GPC under the same conditions as in Synthesis Example 1 was found to be 53000. The powder is designated as copolymer (B).

Synthesis Example 3

12.6 g of MPC, 8.6 g of BMA, and 6.0 g of GMA (MPC/BMA/GMA=30/40/30 (by molar ratio)) were dissolved in 358 g of isopropanol, placed in a four-neck flask, and bubbled with nitrogen for 30 minutes. 2.18 g of a toluene solution of 20 wt % t-butyl peroxypivalate was added at 60° C., and reacted for polymerization for 5 hours. The obtained polymer liquid was added dropwise into 3 L of diethyl ether under stirring, and the resulting precipitate was recovered by filtration, and vacuum dried at room temperature for 48 hours, to obtain 28.4 g of powder. Compositional analysis of the powder by $^1$H-NMR revealed that MPC/BMA/GMA=30/40/30 (by molar ratio). The weight average molecular weight measured by GPC under the same conditions as in Synthesis Example 1 was found to be 42000. The powder is designated as copolymer (C).

Example 1-1

0.5 g of copolymer (A) synthesized in Synthesis Example 1 was dissolved in 100 mL of ethanol to prepare a copolymer solution. 0.3 mL of the copolymer solution was introduced into each well of a U-bottom 96-well plate made of polystyrene, and then aspirated away. The plate was dried under reduced pressure at 50° C. for 5 hours to give vessel (A) for embryoid formation.
The P/C value on the well surface having a coating layer of copolymer (A) of the vessel (A) for embryoid formation was measured. The result is shown in Table 1.

Example 1-2

A U-bottom 96-well plate made of polystyrene was subjected to corona treatment in the air at the irradiation energy of J/cm$^2$ to generate carboxyl groups on the surface. 0.5 g of copolymer (B) synthesized in Synthesis Example 2 was dissolved in 100 mL of isopropanol to prepare a copolymer solution. 0.3 mL of the copolymer solution was introduced into each well of the corona treated, U-bottom 96-well plate, and then aspirated away. The carboxyl groups on the plate surface were reacted with the epoxy groups of the copolymer at 60° C. for 3 hours. 0.3 mL of a 0.2 M sodium thiosulfate aqueous solution was introduced into each well, and reacted at 25° C. for 24 hours for ring-opening the unreacted epoxy. Each well was washed three times with distilled water, and dried under reduced pressure at 50° C. for 5 hours to prepare vessel (B) for embryoid formation.
The P/C value on the well surface having a coating layer of copolymer (B) of the vessel (B) for embryoid formation was measured. The result is shown in Table 1.

Example 1-3

Vessel (C) for embryoid formation was prepared in the same way as in Example 1-2, except that copolymer (B) was replaced with copolymer (C) synthesized in Synthesis Example 3.
The P/C value on the well surface having a coating layer of copolymer (C) of vessel (C) for embryoid formation was measured. The result is shown in Table 1.

Comparative Example 1

The P/C value on the well surface of an untreated, U-bottom 96-well plate made of polystyrene was measured. The result is shown in Table 1.

TABLE 1

| | Vessel | P/C ratio |
|---|---|---|
| Example 1-1 | Vessel (A) for embryoid formation | 0.038 |
| Example 1-2 | Vessel (B) for embryoid formation | 0.074 |
| Example 1-3 | Vessel (C) for forming embryoid bodes | 0.038 |
| Comparative Example 1 | Untreated plate | 0.000 |

Example 2-1

Each well of vessel (A) for embryoid formation prepared in Example 1-1 was plated with 0.2 mL of a suspension of mouse ES cells containing $2\times10^4$ cells/mL prepared in accordance with the following process. After culture at 37° C. in 5% $CO_2$ for 5 days, the development of embryoid bodies was observed under a phase contrast microscope. The result is shown in Table 2. A photocopy of the phase contrast micrograph is shown in FIG. 1.
In Table 2, the development of embryoid bodies was evaluated and indicated as A when an embryoid body of sufficient size for differentiation was formed; B when an embryoid body was formed but not of a sufficient size; and C when no embryoid body was formed.
<Preparation of Suspension of Mouse ES Cells>
(1) Culture of Feeder Cells
As feeder cells, SIM mouse fibroblasts (abbreviated as STO cells hereinbelow) were used. The STO cells were cultured in Dulbecco's modified Eagle's medium (abbreviated as DMEM medium hereinbelow, manufactured by GIBCO) supplemented with 25 units/mL of penicillin, 25 g/mL of streptomycin, and 10 vol % of immobilized fetal calf serum (FCS). The cultured STO cells were treated with a 10 g/mL mitomycin C solution (manufactured by SIGMA) for 3 hours, and a cell suspension was prepared. The STO cell suspension, containing $5 \times 10^5$ cells, was plated in each well of a 6-well multidish, and cultured at 37° C. in 5% $CO_2$ for 16 hours to prepare feeder cells.

(2) Culture of Mouse ES Cells

As ES cells, 129V mouse ES cells were used. The medium for ES cells was a DMEM medium supplemented with 15% Knock Out (trade mark) serum replacement (KSR: manufactured by GIBCO), 1 mM sodium pyruvate (manufactured by GIBCO), 0.1 mM nonessential amino acids (manufactured by GIBCO), 0.1 mM 2-mercaptoethanol (manufactured by SIGMA), 25 units/mL of penicillin, 25 g/mL of streptomycin, and 1000 units/mL of murine leukemia inhibitory factor (mLIF: manufactured by CHEMICON) (abbreviated as ES medium hereinbelow). $2 \times 10^5$ cells/well of the ES cells were plated on the feeder cells prepared in paragraph (1) above, and cultured at 37° C. in 5% $CO_2$ for 3 days.

The mouse ES cells cultured in paragraph (2) above were released by a common procedure using 0.1% trypsin-EDTA, and suspended in an IMDM medium (manufactured by GIBCO, without mLIF) supplemented with 15% FCS, 0.1 mM 2-mercaptoethanol (manufactured by SIGMA), 25 units/mL of penicillin, and 25 g/mL of streptomycin, to prepare a suspension of mouse ES cells at a concentration of $2 \times 10^4$ cells/mL.

Examples 2-2 and 2-3

The experimental procedures of Example 2-1 were followed, except that vessel (A) for embryoid formation was replaced with vessel (B) or (C) for embryoid formation prepared in Example 1-2 or 1-3, respectively. The results are shown in Table 2.

Comparative Example 2-1

Figure 2:
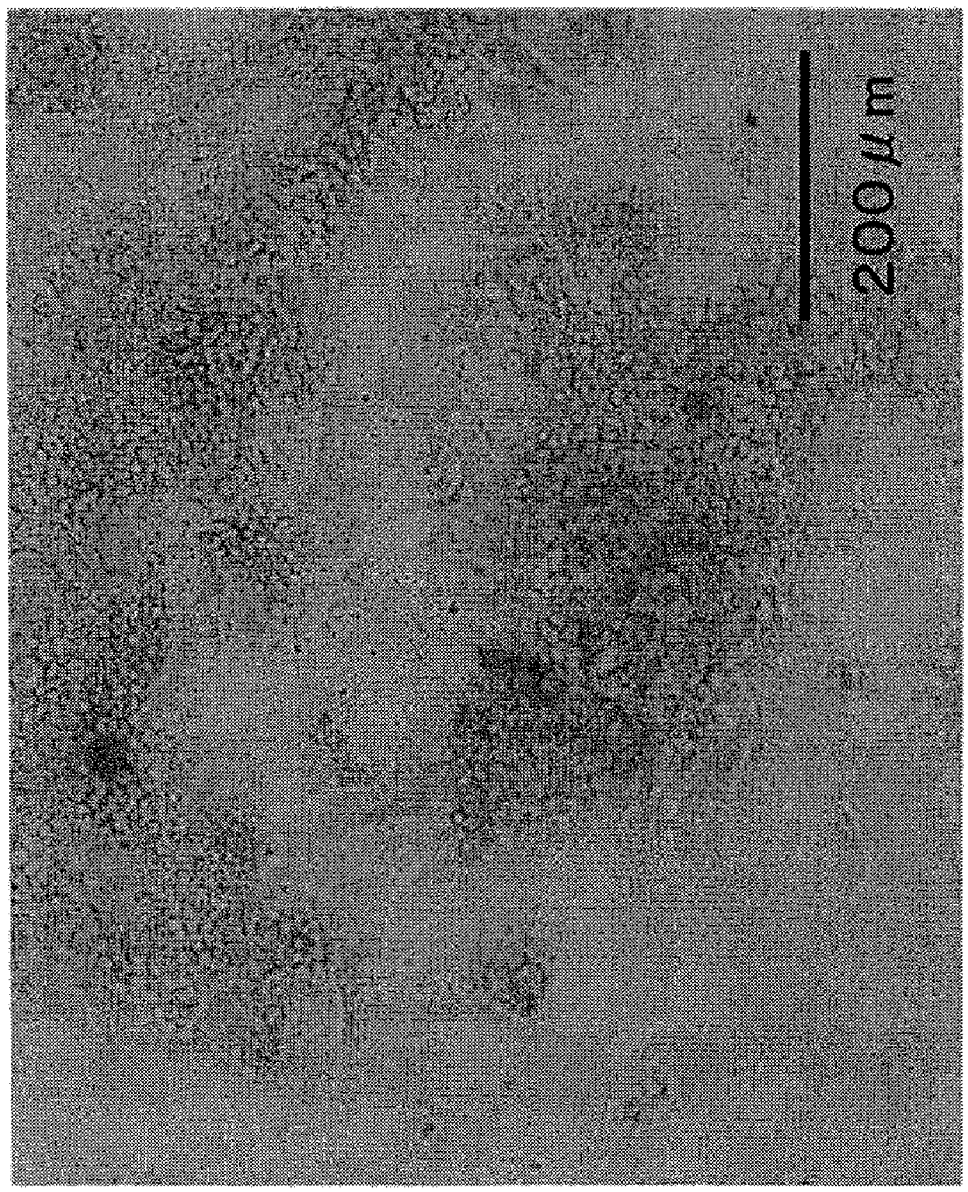
FIG. 2 is a photocopy of a phase contrast micrograph of an embryoid body cultured in Comparative Example 2-1 using an untreated plate.

The experimental procedures of Example 2-1 were followed, except that vessel (A) for embryoid formation was replace with an untreated 96-well polystyrene plate. The result is shown in Table 2. Further, the development of embryoid bodies was observed under a phase contrast microscope. A photocopy of the phase contrast micrograph is shown in FIG. 2. followed, except that vessel (A) for embryoid formation was replace with an untreated 96-well polystyrene plate. The result is shown in Table 2. Further, the development of embryoid bodies was observed under a phase contrast microscope. A photocopy of the phase contrast micrograph is shown in FIG. 2.

Comparative Example 2-2

Figure 3:
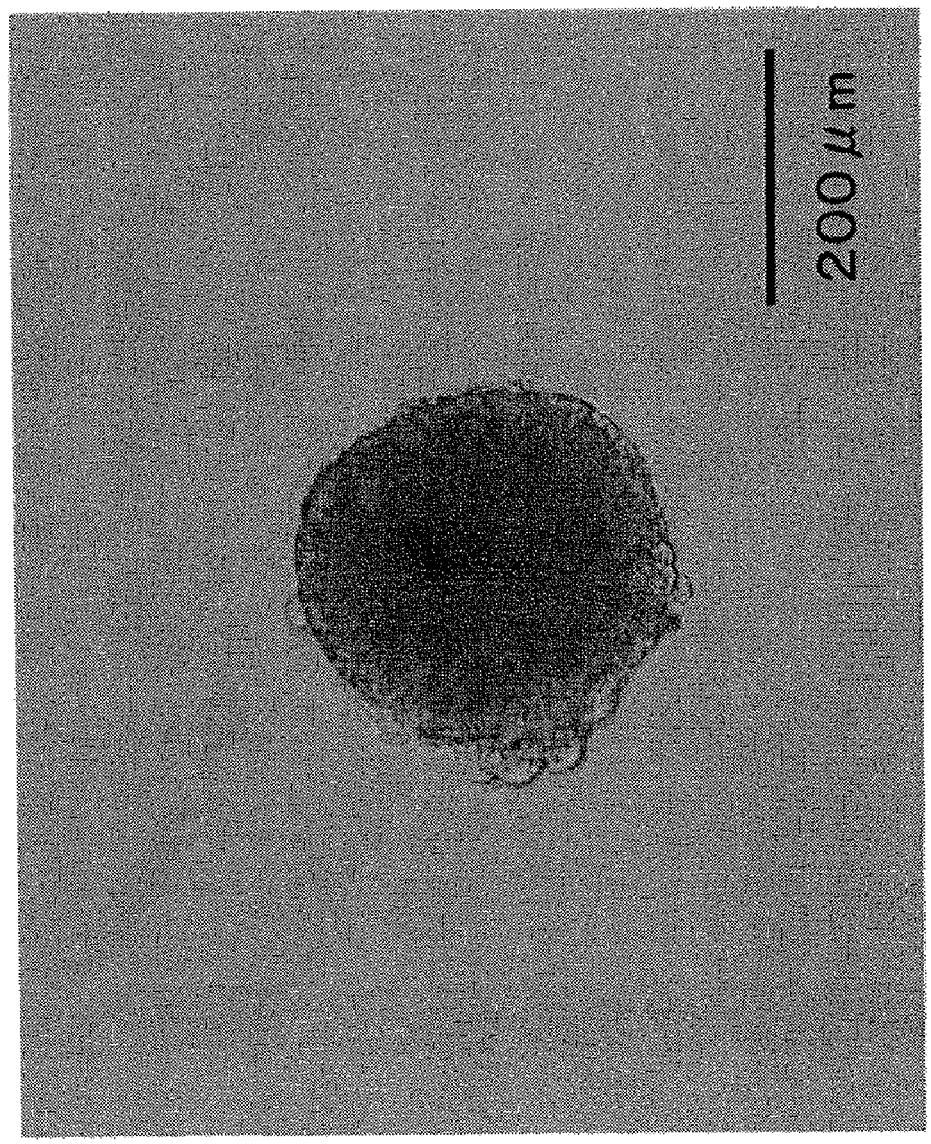
FIG. 3 is a photocopy of a phase contrast micrograph of an embryoid body formed by the hanging drop method in Comparative Example 2-2.

130 μL of phosphate buffer and 200 μL of mineral oil were introduced in advance in each well of a flat bottom 96-well plate made of polystyrene, and then 50 μL of the $2 \times 10^4$ cells/mL suspension of mouse ES cells prepared above was plated in each well. After culture at 37° C. in 5% $CO_2$ for 5 days, the resulting embryoid bodies were transferred to a U-bottom 96-well plate made of polystyrene. Then phase contrast microscopic observation was made in the same way as in Example 2-1. The result is shown Table 2. A photocopy of the phase contrast micrograph is shown in FIG. 3.

Comparative Example 2-3

The experimental procedures of Example 2-1 were followed, except that vessel (A) for embryoid formation was replaced with SUMILON celltight spheroid (trade mark, 96-well plate, manufactured by SUMITOMO BAKELITE CO., LTD.) The result is shown in Table 2.

TABLE 2

| | Vessel | Formation of embryoid bodies |
|---|---|---|
| Example 2-1 | Vessel (A) for embryoid formation | A |
| Example 2-2 | Vessel (B) for embryoid formation | A |
| Example 2-3 | Vessel (C) for embryoid formation | A |
| Comparative Example 2-1 | Untreated plate | C |
| Comparative Example 2-2 | Hanging drop method | B |
| Comparative Example 2-3 | Spheroid plate | B |

Examples 3-1 to 3-3

The embryoid bodies prepared in Examples 2-1 to 2-3 were pipetted with 0.1 mL of the medium, and transferred to a gelatin-coated dish prepared by the following process. Half of the medium was changed every 3 days. After culture at 37° C. in 5% $CO_2$ for 7 days, phase contrast microscopic observation was made. The results are shown in Table 3.

In Table 3, the differentiation into cardiomyocyte was evaluated and indicated as A when beating cardiomyocytes were observed; B when a few beating cardiomyocytes were observed; and C when the operation was not possible.

<Preparation of Gelatin-Coated Dish>

A 0.1 wt % aqueous solution of gelatin previously sterilized by autoclaving at 121° C. for 20 minutes, was uniformly spread over a 24-well culture multidish. The multidish was refrigerated, and the gelatin solution was aspirated with an aspirator immediately before use. 1 mL of IMDM medium (manufactured by GIBCO, without mLIF) supplemented with 15% FCS, 0.1 mM 2-mercaptoethanol (manufactured by SIGMA), 25 units/mL of penicillin, and 25 g/mL of streptomycin, was added to each well.

Comparative Example 3-1

The cells adhered to the plate bottom in Comparative Example 2-1 were tried to be transferred to a gelatin-coated dish, but were not successful.

Comparative Examples 3-2 and 3-3

The experimental procedures of Example 3-1 were followed, except that the embryoid bodies prepared in Comparative Examples 2-2 (Comparative Example 3-2) and 2-3 (Comparative Example 3-3) were used. The results are shown in Table 3.

TABLE 3

| | Vessel | Differentiation into cardiomyocytes |
|---|---|---|
| Example 3-1 | Vessel (A) for embryoid formation | A |
| Example 3-2 | Vessel (B) for embryoid formation | A |
| Example 3-3 | Vessel (C) for embryoid formation | A |

TABLE 3-continued

| | Vessel | Differentiation into cardiomyocytes |
|---|---|---|
| Comparative Example 3-1 | Untreated plate | C |
| Comparative Example 3-2 | Hanging drop method | B |
| Comparative Example 3-3 | Spheroid plate | B |

Table 1 shows that the P/C values in Examples 1-1 to 1-3 are in the range of 0.038 to 0.074. This indicates that vessels (A) to (C) for embryoid formation were coated with a coating layer of a polymer having a PC-like group. Table 2 indicates that culture of mouse ES cells in vessels (A) to (C) for embryoid formation results in good formation of embryoid bodies. Table 3 indicates that the embryoid bodies formed from mouse ES cells in vessels (A) to (C) for embryoid formation have excellent ability to differentiate into cardiomyocytes.

Further, from FIG. 1, it is understood that use of the vessel for embryoid formation according to the present invention results in formation of embryoid bodies of sufficient size for differentiation. From FIG. 2, it is understood that use of the untreated polystyrene vessel results in no formation of embryoid bodies. From FIG. 3, it is understood that the embryoid bodies formed by the hanging drop method is not of sufficient size.

What is claimed is:

1. A method for forming embryoid bodies comprising the steps of:
    (A) providing a vessel for embryoid formation having a coating layer formed from a copolymer of monomer (M) represented by the formula (1) having a phosphorylcholine-like group and another monomer, on a vessel surface defining a region for floating-culture of embryonic stem cells:

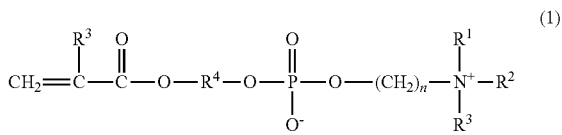

(1)

wherein $R^1$, $R^2$, and $R^3$ are the same or different groups, and each of said $R^1$, $R^2$, and $R^3$ stands for a hydrogen atom, an alkyl or hydroxyalkyl group having 1 to 6 carbon atoms; $R^4$ stands for an alkyl group having 1 to 6 carbon atoms; $R^5$ stands for a hydrogen atom or a methyl and n is an integer of 1 to 4; and
    (B) floating-culturing embryonic stem cells in said vessel for embryoid formation to form embryoid bodies.

2. The method of claim 1, wherein a ratio (P/C) of the amount of phosphorus element P to the amount of carbon element C as measured by X-ray photoelectron spectroscopy on the vessel surface having said coating layer formed thereon is 0.002 to 0.3.

3. The method of claim 1, wherein said monomer (M) is selected from the group consisting of 2-((meth)acryloyloxy)ethyl-2'-(trimethylammonio)ethylphosphate, 3-((meth)acryloyloxy)propyl-2'-trimethylammonio)ethylphosphate, 4-((meth)acryloyloxy)butyl-2'-(trimethylammonio) ethylphosphate, 5-((meth)acryloyloxy)pentyl-2'-(trimethylammonio)ethylphosphate, 6-((meth)acryloyloxy)hexyl-2'-(trimethylammonio)ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethylphosphate, 2-((meth)acryloyloxy)propyl-2'-(trimethylammonio) ethylphosphate, 2-((meth)acryloyloxy) butyl-2'-(trimethylammonio)ethylphosphate, 2-((meth)acryloyloxy)pentyl-2'-(trimethylammonio)ethylphosphate, and 2-((meth) acryloyloxy)hexyl-2'-(trimethylammonio) ethylphosphate.

4. The method of claim 1, wherein said another monomer is selected from the group consisting of methyl(meth)acrylate, ethyl(meth)acrylate, butyl(meth)acrylate, 2-ethylhexyl (meth)acrylate, lauryl(meth)acrylate, stearyl(meth)acrylate, cyclohexyl(meth)acrylate, benzyl(meth)acrylate, phenoxyethyl(meth)acrylate, polypropylene glycol(meth)acrylate, styrene, methylstyrene, chloromethylstyrene, methyl vinyl ether, butyl vinyl ether, vinyl acetate, vinyl propionate, 2-hydroxyethyl(meth)acrylate, 2-hydroxybutyl (meth)acrylate, 4-hydroxybutyl(meth)acrylate, acrylic acid, methacrylic acid, styrenesulfonic acid, (meth)acryloyloxyphosphonic acid, 2-hydroxy-3-(meth)acryloyloxypropyl trimethyl ammonium chloride, (meth)acrylamide, aminoethylmethacrylate, dimethylaminoethyl(meth)acrylate, polyethylene glycol (meth)acrylate, glycidyl (meth)acrylate, and mixtures thereof.

5. The method of claim 1, wherein the weight average molecular weight of said copolymer is 5000 to 5000000.

6. The method of claim 1, wherein said monomer (M) is 2-(methacryloyloxy)ethyl-2'-(trimethylammonio)ethylphosphate, and said another monomer is at least one of butyl(meth) acrylate and glycidyl (meth)acrylate.

* * * * *